(12) United States Patent
Azuma

(10) Patent No.: US 8,333,699 B2
(45) Date of Patent: Dec. 18, 2012

(54) ULTRASONOGRAPH

(75) Inventor: Takashi Azuma, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 218 days.

(21) Appl. No.: 12/671,377

(22) PCT Filed: Feb. 15, 2008

(86) PCT No.: PCT/JP2008/052521
§ 371 (c)(1),
(2), (4) Date: Jan. 29, 2010

(87) PCT Pub. No.: WO2009/031327
PCT Pub. Date: Mar. 12, 2009

(65) Prior Publication Data
US 2010/0191111 A1    Jul. 29, 2010

(30) Foreign Application Priority Data
Sep. 6, 2007   (JP) ................................ 2007-230902

(51) Int. Cl.
*A61B 8/00*   (2006.01)
(52) U.S. Cl. ......................... 600/438; 600/407; 600/437
(58) Field of Classification Search .................. 600/407, 600/437–438; 382/128
See application file for complete search history.

(56) References Cited

U.S. PATENT DOCUMENTS

| | | | |
|---|---|---|---|
| 4,768,515 A | 9/1988 | Namekawa | |
| 6,508,768 B1 * | 1/2003 | Hall et al. | 600/443 |
| 2003/0220554 A1 * | 11/2003 | Grenon et al. | 600/407 |
| 2006/0052696 A1 | 3/2006 | Shiina et al. | |
| 2008/0081993 A1 | 4/2008 | Waki | |
| 2008/0285819 A1 * | 11/2008 | Konofagou et al. | 382/128 |

FOREIGN PATENT DOCUMENTS

| | | |
|---|---|---|
| JP | 62-152439 | 7/1987 |
| JP | 10-258052 | 9/1998 |
| JP | 2004-057653 | 2/2004 |
| JP | 2004-283518 | 10/2004 |
| JP | 2006-325704 | 12/2006 |
| WO | WO 2006/073088 A1 | 7/2006 |

* cited by examiner

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

An ultrasonograph is provided which, when a difference occurs between an expected tissue displacement direction and a displacement estimation direction, minimizes errors caused by the difference to improve accuracy of an elasticity image. The ultrasonograph includes: an ultrasound probe to emit an ultrasound in a plurality of mutually crossing directions against a subject; an ultrasound transmit and receive part to control the ultrasound probe to perform a plurality of transmissions and receptions of the ultrasound in each of the plurality of directions; a displacement vector processor to calculate a displacement vector in each of the plurality of directions from a result of the plurality of transmissions and receptions; a strain processor to calculate strain information of the subject based on the displacement vectors; an image data generator to create image data based on the calculated strain information; and a display to display an image based on the image data.

17 Claims, 13 Drawing Sheets

ULTRASONOGRAPH

INCORPORATION BY REFERENCE

The application claims the priority benefit of Japanese Patent Application No. 2007-230902, filed on Sep. 6, 2007, the entire descriptions of which are incorporated herein by reference.

TECHNICAL FIELD

This invention relates to an ultrasound imaging technique to create an elasticity image showing properties of biological tissues of a subject such as their strains and hardness.

BACKGROUND ART

An ultrasound diagnostic apparatus to produce an ultrasound image transmits an ultrasound from an ultrasound probe to a subject, receives an echo from the subject by the ultrasound probe, reconstructs an ultrasound image based on signals received from the ultrasound probe and displays the reconstructed image.

As one such ultrasound diagnostic apparatus, there has been known an apparatus that creates an elastic image revealing properties of living tissues of a subject, such as strains and hardness. For example, the ultrasound diagnostic apparatus acquires time-sequenced images of a living tissue as the subject is applied a pressure, measures a displacement of the tissue by taking a cross-correlation among the acquired time-sequenced images and determines elasticity data (e.g., strain and elasticity modulus) based on the measured displacement (e.g., Patent document 1). In measuring the displacement of a living tissue, one method of applying a pressure to the subject may involve, for example, manually pushing the ultrasound probe against the subject with a force.

A point spread function in ultrasound imaging is normally short in an ultrasound propagation direction and spread in a direction perpendicular to the propagation direction (the latter direction is hereinafter referred to as a lateral direction). So, a local displacement measurement is done only in the propagation direction and not in the lateral direction. In practice, there is a case where a direction in which a living tissue is actually displaced when a pressure is applied to the subject (hereinafter referred to as a tissue displacement direction) may not be parallel to an elasticity calculation direction in which the displacement of the living tissue is measured (hereinafter referred to as a displacement estimation direction). That is, the displacement estimation direction is fixedly set in a direction perpendicular to an ultrasound transmission/reception surface, whereas the tissue displacement direction changes unstably depending on the direction in which the tissue is pressurized or the shape of a pressing surface. To adjust with this situation, a method is available which matches the displacement estimation direction with the tissue displacement direction (e.g., Patent document 2).

Patent document 1: JP-A-2004-57653
Patent document 2: WO 2006/073088

DISCLOSURE OF INVENTION

Problem to be Solved by the Invention

When a living tissue makes complex movements, a difference may occur between an expected tissue displacement direction and a displacement estimation direction. For example, if, on the far side of the tissue of interest, there lies an area whose hardness may change, such as bones, tracheae and intestinal tracts or if there is a sliding surface, or if a pressure is applied by the ultrasound probe to the tissue of interest, a complex movement will result. Also if there is a sliding surface (such as an organ boundary surface) between a pressure source and a portion being measured, the direction of movement easily becomes unstable. If under such conditions an elasticity image is constructed of the measured values, the elasticity image may not faithfully reveal the property of the living tissue as it makes complex movements.

Means for Solving the Problem

The ultrasonograph of this invention, as one example, comprises: an ultrasound probe to emit an ultrasound in a plurality of mutually crossing directions against a subject; an ultrasound transmit and receive part to control the ultrasound probe to perform a plurality of transmissions and receptions of the ultrasound in each of the plurality of directions; a displacement vector processor to calculate a displacement vector in each of the plurality of directions from a result of the plurality of transmissions and receptions of the ultrasound; a strain processor to calculate strain information of the subject based on the displacement vectors; an image data generator to create image data based on the calculated strain information; and a display to display an image based on the image data.

ADVANTAGES OF THE INVENTION

When there is a difference between an expected tissue displacement direction and a displacement estimation direction, this invention can reduce errors caused by the difference, thereby improving accuracy of an elasticity image.

Other objects, features and advantages of this invention will become apparent from the following descriptions of examples embodying the invention.

Embodiments

Embodiments of the present invention will be described in the following.

(Embodiment 1)

Scanning in two directions can be achieved by the following three methods.

I. An aperture is formed that transmits and receives a beam in a direction of angle "a"; transmission and reception is performed; and the aperture is moved to execute a first scan. This is followed by another aperture being formed that transmits a beam in a direction of angle "−a"; transmission and reception is performed; and the aperture is moved to perform a second scan. This method is similar to the angle direction compound method.

II. An aperture is formed that transmits and receives a beam in a direction of angle "a"; transmission and reception is performed; and then transmission and reception is performed in a direction of angle "−a". An aperture is formed, transmission and reception performed, and the aperture moved. After the aperture is moved, transmission and reception is done in the directions of angle "a" and angle "−a". The transmission/reception and the aperture movement are repeated until the scan reaches the end of a scan area.

III. The aperture is divided into a sub-aperture 1 for transmitting a beam in a direction of angle "a" and a sub-aperture 2 for transmitting a beam in a direction of angle "−a". Transmission and reception is performed with the sub-apertures 1, 2 successively. Next, the aperture as a whole is shifted in position. This is followed by the aperture being divided again to perform the transmission and reception. This sequence of operation is repeated. At this time, the subapertures may be obtained by simply dividing the original aperture at the center, or by dividing elements into groups of even-numbered elements and odd-numbered ones.

The methods I and II use a large aperture and therefore can create a beam with relatively small artifacts. Of these two, the method II can reduce influences of movements of a subject when compared with the method I. That is, the total imaging time is the same for the two methods I, II.

It is noted, however, that whereas in the method I, the "a"-direction imaging and the "-a"-direction imaging are completely separate in time, the method II has the time window of the "-a"-direction imaging partly overlap the time window of the "a"-direction imaging. This means the two imaging operations in the method II are not completely separate from each other, resulting in the motion-based artifacts being hardly apparent in some cases. As to the method III, if the angle "a" beam and the angle "-a" beam are separate from each other to an enough degree (spatial overlapping of the two beams is small enough) to allow simultaneous transmission and reception, the frame rate can be improved. This in turn reduces the effects of movements of a subject.

While the above methods I, II, III have been described for the two-dimensional imaging, they can also be applied to a three-dimensional imaging with some adaptations.

An embodiment of an ultrasound diagnostic apparatus and an ultrasound imaging method applying the present invention will be described by referring to the accompanying drawings. FIG. 1 is a block diagram of an ultrasonograph of this embodiment. FIG. 2 is a diagram showing a process flow of FIG. 1.

As shown in FIG. 1, the ultrasonograph comprises an ultrasound probe (hereinafter referred to as a probe 102) to send and receive ultrasounds to and from a subject 101; an ultrasound transmit and receive part 103 to supply a drive signal to the probe 102 for wave transmission and process a received signal output from the probe 102; an elasticity image processor 100 to generate image data based on displacements of biological tissues that are measured using the output signal of the ultrasound transmit and receive part 103 and create an elasticity image; and a display 112 as a means to display the elasticity image obtained. The elasticity image processor 100 here comprises a displacement vector processor 105, a displacement scalar processor 106, a strain processor 107, an elastic modulus (elasticity) processor 108 and a color digital scan converter 109 (hereinafter referred to as a color DSC 109). There is a controller 113 to issue a control command to the ultrasound transmit and receive part 103 and the elasticity image creating means. Here, the ultrasound transmit and receive part 103 supplies a drive signal to the probe 102 to cause it to transmit ultrasounds in at least two directions that cross each other, as described below.

The two-direction ultrasound transmission is explained by referring to FIG. 5. In the ultrasound imaging by an electronic scan using a phased array probe, the control of delay time among devices allows ultrasounds to be transmitted and received not only in a frontal direction of the devices but also in a direction deflected through an angle θ from the frontal direction. Here, a direction 503, which is at an angle of −θ to a direction 502 (same as the propagation direction) perpendicular to a surface 501 of the device facing the subject, is taken as a first measurement direction (direction of measured vector 1). With this steering, a frame 1 is imaged a plurality of times (for example, twice) and a displacement in the direction of angle −θ (the direction of displacement estimation vector 1) is determined according to the correlation between the frames. Next, a direction 504, which is at an angle of +θ to a direction 502 perpendicular to a surface 501 of the device facing the subject is taken as a second measurement direction (direction of measured vector 2). With this steering, a frame 2 is imaged a plurality of times (for example, twice) and a displacement in the direction of angle +θ (direction of displacement estimation vector 2) is determined according to the correlation between the frames. The measured vector 1 and the measured vector 2 are added up to determine a two-dimensional displacement vector corresponding to the two-dimensional strain. As shown in FIG. 6, where the measured vector 1 is perpendicular to the measured vector 2, the two-dimensional displacement vector can easily be obtained by adding the two measured vectors. However, setting too large a steering angle in the ultrasound imaging gives rise to a possibility of artifacts produced by a grating beam becoming large. Thus the steering angle may be set at less than 45 degrees, preferably between 20 degrees and 30 degrees. It is also possible to draw an auxiliary line in a direction perpendicular to each of the two measured vectors to find an intersection, thus determining a two-dimensional displacement vector with its end point at the intersection.

Next, the process flow will be explained by referring to FIG. 2. First, image data in the measurement direction 1 is retrieved (201). Next, image data in the measurement direction 1 is picked up again (202). Based on the cross-correlation between the image data obtained in these two steps, a displacement in the direction 1 is calculated (203). Here, the cross-correlation between functions $f_1(x)$ and $f_2(x)$ is given by $\int f_1(v) f_2^*(v-x) dv$. Next, image data in the measurement direction 2 is acquired (204). Then, image data in the measurement direction 2 is again obtained (205). Based on the cross-correlation between the image data acquired in these two steps, a displacement in the direction 2 is calculated (206). From the displacements in the measurement direction 1 and the measurement direction 2 acquired in step 203 and step 206, a two-dimensional displacement vector is determined (207). The two-dimensional displacement vector obtained in step 207 is used to calculate the magnitude of an absolute value of the displacement (208). From the absolute value of the displacement, calculation is made of a strain (209) and an elastic modulus (210). Here, if we let the displacement be $\Delta L$, since the strain S is a spatial differential of the displacement, it can be determined as $S = \Delta L / \Delta x$. Although the differential of data scattered in the spatial direction can be calculated as a convolution with a differential filter having a coefficient of [1, −1], it is effective to put a low-pass filter before or after the differential to remove noise, because the differential is easily affected by noise. The elastic modulus E can be calculated as $E = \Delta P / S$, assuming the stress $\Delta P$ is uniform.

Therefore, even if the direction of displacement estimation is not specified, the displacement along the tissue displacement direction can be calculated by determining a plurality, at least two, of measurement directions. This improves the precision of the measured values. Constructing an elasticity image based on these measured values allows the properties of live tissues to be shown precisely in the elasticity image.

Next, merits of the above construction will be explained. If an ultrasound is not emitted in a plurality, at least two, of measurement directions, but instead emitted in the direction 1, the displacement to be calculated in a displacement computation unit is a one-dimensional displacement. FIGS. 3A and 3B show point spread functions in the propagation direction and in the lateral direction for an ultrasound of 7.5 MHz. FIG. 3A shows a relative sensitivity in the propagation direction with respect to the propagation direction. FIG. 3B shows a relative sensitivity in the lateral direction with respect to the lateral direction. As to the propagation direction, time is converted into a distance in the propagation direction by taking the speed of sound to be 1540 m/s. (It is noted that, for the purpose of calculation in the transmission and reception, time is multiplied by the speed of sound and the round-trip distance is divided in half.) Here, an arrow represents a distance of one wavelength. The lateral direction represents a width of a beam. As weight functions, a solid line represents a rectangular weight and a dashed line represents a Gaussian weight. Ordinates in both graphs represent an amplitude of the point spread functions. The width represents a beam width. As shown in FIGS. 3A and 3B, while the point spread function of ultrasounds shows a sharp change in the propagation direction, its change in the lateral direction is moderate. Therefore, a displacement detection limit in the propagation direction and a detection limit in the lateral direction differ by a factor of between about 6 and 10. In the elastic modulus imaging, a pressure is applied in the propagation direction and then the elastic modulus is estimated by dividing the pressure by a strain. After the one-dimensional displacement has been determined, the displacement is spatial-differentiated to determine a strain and, with the pressure assumed to be uniform, an amount proportional to the elastic modulus is calculated. That is, the difference between FIG. 1 and the case of emitting a wave in the direction 1 is whether the displacement is estimated in one direction only or in a plurality of directions (in FIG. 1, two directions).

Advantages of measuring a displacement in a plurality of directions will be explained by referring to FIGS. 4A and 4B. If the displacement caused by the application of pressure to a tissue and the propagation direction of an ultrasound is virtually parallel, there is no shift between the displacement direction and the propagation direction. So, in parts of a subject where tissues can easily be moved by the application of pressure in the direction of propagation of the ultrasound (e.g., mammary gland and prostate), such a shift does not easily occur. On the other hand, where a cross section of an artery, such as shown in FIG. 4A, is to be imaged so as to be accommodated within a slice, with pulsations of the artery as a pressure source, or where, as shown in an elastic modulus image of a thyroid of FIG. 4B, the structure within a body on a far side of the subject part from the probe is not uniform, the uniformity of the tissue displacement may be lost. In such a case, if the displacement is determined only in the ultrasound propagation direction, i.e., in the direction of displacement estimation, a local value greater than the real elastic modulus may be obtained. In other words, measuring a displacement in a plurality of directions allows the displacement of a tissue to be acquired as two-dimensional information, leading to a more precise measurement of the displacement.

Now, more detailed explanation of the embodiment of the ultrasonograph will be given as follows. The ultrasonograph is largely divided into an ultrasound transmit and receive system, a B-mode imaging system, an elasticity imaging system, a display system and a control system. The ultrasound transmit and receive system has a probe 102 and an ultrasound transmit and receive part 103. The probe 102 has an ultrasound transmit and receive surface that mechanically or electronically performs a beam scan to send and receive the ultrasound to and from the subject 101. The ultrasound transmit and receive surface has a plurality of oscillators arrayed thereon. Each of the oscillators performs a mutual conversion between an electric signal and an ultrasound.

The ultrasound transmit and receive part 103 has a transmission means to supply a drive signal (pulse) for ultrasound transmission to the probe 102 through a transmit and receive means, and a reception means to process a received signal output from the probe 102 through the transmit and receive means.

The transmission means of the ultrasound transmit and receive part 103 has a circuit that transmits at a predetermined interval a transmission pulse as a drive signal for generating ultrasound by driving the oscillators of the probe 102. The transmission means also has a circuit that sets a depth of a focus point of the ultrasound beam emitted from the probe 102. The transmission means of this embodiment selects a group of oscillators that supplies pulses through the transmit and receive means, and at the same time controls the timing at which the transmission pulse is produced so that the ultrasound beam emitted from the probe 102 scans in the tissue displacement direction. That is, the transmission means controls the direction of scan of the ultrasound beam by controlling the delay time of the pulse signal.

The reception means of the ultrasound transmit and receive part 103 has a circuit that amplifies with a predetermined gain a signal output from the probe 102 through the transmit and receive means to create an RF signal or received echo signal, and a circuit that performs a phased addition of the RF signals to create RF signal data time-sequentially. This reception means performs the phased addition by giving a predetermined delay time to the echo signals received from the ultrasound beam emitted from the probe 102 through the transmit and receive means to align the phases.

The B-mode imaging system has a B-mode image processor 104. The B-mode image processor 104 has a signal processor and a grayscale scan converter. The signal processor performs image processing on the RF signal output from the ultrasound transmit and receive part 103 to create a grayscale B-mode image data (e.g., grayscale B-mode image data). The image processing performed here includes a gain correction, log compression, detection, outline enhancement and filter processing. The grayscale scan converter reads the B-mode image data on the subject 101 stored in a frame memory, one frame at a time, and outputs the read-out B-mode image data in synchronism with television. The grayscale scan converter here has an A/D converter to convert the B-mode image data output from the signal processor into a digital signal, a frame memory to store a plurality of pieces of digitized B-mode image data in a time sequence, and a controller to issue a command to read the B-mode image data from the frame memory.

The elasticity imaging system has a displacement vector processor 105 branching from the output side of the ultrasound transmit and receive part 103, a displacement scalar processor 106, a strain processor 107, an elasticity processor 108 and a color DSC 109.

The displacement vector processor 105 measures the displacement of a tissue of the subject 101 based on the RF signal data output from the ultrasound transmit and receive part 103. The displacement vector processor 105 has an RF signal selection part, a computation part and a filtering part. What is characteristic of this processor is that it performs the displacement calculation two times by changing the steering angle.

The RF signal selection part of the displacement vector processor 105 has a frame memory and a selection part. The RF signal selection part stores in the frame memory the time-sequenced RF signal data output from the ultrasound transmit and receive part 103 and then chooses from the stored RF signal frame data group two sets, i.e., four pieces, of RF signal frame data by the selection part. More specifically, the RF signal selection part successively secures in the frame memory the time-sequenced RF signal data output from the ultrasound transmit and receive part 103 according to an image frame rate. Then, the RF signal selection part, in response to the command issued from the controller 113, selects RF signal frame data (N) as first data from among the RF signal data group stored in the frame memory. Next, the RF signal selection part, in response to the command issued from the controller 113, selects RF signal frame data (X) as second data from among the RF signal data group stored in the frame memory. Here, the RF signal frame data (X) has been chosen from among the RF signal frame data group (N-1, N-2, N-3, N-M) that was stored in the frame memory before the RF signal frame data (N). N, M and X are natural numbers that are related, as index numbers, to the RF signal frame data.

The computation part of the displacement vector processor 105 first determines the displacement of a tissue in the displacement estimation direction from one set of RF signal frame data with equal steering angles. More specifically, the computation part executes a one- or two-dimensional correlation operation between the first RF signal frame data (N) and the second RF signal frame data (X) picked up by the RF signal selection part. For the correlation operation the computation part may use, for example, the block matching technique to determine the displacement of a tissue in the displacement estimation direction for each pixel in the B-mode image and also a movement vector (hereinafter generally referred to as displacement). The movement vector mentioned here refers to a one- or two-dimensional displacement distribution in terms of direction and magnitude of displacements. The block matching technique is an operation that involves dividing an image into blocks of, for instance, NXN pixels, focusing on one block in an area of interest, searching through older frames for a block resembling the one being watched and, by referring to the searched block, determining a sample value based on a prediction encoding or difference. Then, from one set of RF signal frame data measured at a different steering angle, the displacement of a tissue in the displacement estimation direction is determined for another direction. With these two processes, the computation of the two-dimensional displacement, i.e., vector displacement, is complete.

The filtering part of the displacement vector processor 105 has a filter circuit for leveling variations in the displacement of a tissue output from the displacement computation part to provide preprocessing for assuring smooth signal processing in a downstream stage. From the amount of vector displacement thus determined, the length of the vector is calculated. Then the amount of displacement as a scalar is calculated by the displacement scalar processor 106.

The strain processor 107 performs a spatial differentiation on the distance that the tissue has moved which has been output from the displacement scalar processor 106, e.g., a displacement $\Delta L$, to determine strain data of the tissue ($S=\Delta L/\Delta X$). The elasticity processor 108 calculates elastic modulus data of the tissue by dividing a pressure change by a displacement change. For example, the elasticity processor 108 acquires from a pressure measuring part a pressure $\Delta p$ applied to the ultrasound transmission and reception surface of the probe 102. Then, the elasticity processor 108 determines a Young's modulus $E=(\Delta p)/S$ as elastic modulus data by using the pressure $\Delta p$ and the displacement $\Delta L$. By determining the elastic modulus data for each point in the B-mode image, as described above, the elasticity processor 108 acquires two-dimensional elasticity image data. The Young's modulus refers to a ratio of a simple tensile stress applied to an object to a strain occurring parallel to the tension. It is noted that the data comprising the strain data and the elastic modulus data is called elasticity data as appropriate, and the elasticity data by frame is referred to as elasticity frame data.

The color DSC 109 constructs a color elasticity image of a tissue of the subject 101 by using the elasticity data output from the strain processor 107 or from the elasticity processor 108. The color DSC 109 has, for example, an elasticity data processor, a color scan converter and a frame memory. The elasticity data processor stores in the frame memory the elasticity frame data output from the strain processor 106 or the elasticity processor 108. The elasticity data processor, in response to a command issued from the controller 113, performs image processing on the elasticity frame data read from the frame memory.

The color scan converter of the color DSC 109 executes a color conversion operation on the elasticity frame data output from the elasticity data processor according to a color map. The color map mentioned above relates color information determined by red (R), green (G) and blue (B) to the magnitude of elasticity data. The red (R), green (G) and blue (B) each have 256 grayscale levels. As they approach 255th level, they are displayed at a higher brightness; and as they move closer to 0th level, their brightness goes down.

For example, the color scan converter of the Color DSC 109 converts the strain data output from the elasticity data processor into a red color code when the strain data is small and, when the strain data is large, into a blue color code before storing them in the frame memory. Then, the color scan converter, in response to a control command, reads the elasticity frame data from the frame memory in synchronism with television and shows it on the display 112. The elasticity image based on the color-converted elasticity frame data is displayed in a way that makes a hard portion of the tissue (e.g., tumor or cancer) look reddish and portions surrounding the hard portion bluish. Such an elasticity image allows the viewer to visually recognize the expanse and size of the tumor. The color DSC 109 is connected with an interface 114, such as a keyboard, through the controller 113. In response to a command issued through the interface 114, the color DSC 109 can change a hue of the color map.

The display system has an image synthesize part 111 and a display 112. The image synthesize part 111 combines a B-mode image output from the B-mode image processor 104 and an elasticity image output from the color DSC 109 into an ultrasound image. For example, the image synthesize part 111 has a frame memory, an image processor and an image selection part. The frame memory stores B-mode images output from the B-mode image processor 104 and elasticity images output from the color DSC 109. The image processor, in response to a control command, reads from the frame memory the B-mode image and the elasticity image. Then, in the B-mode image and the elasticity image that have mutually corresponding pixels in the same coordinate system, the image processor picks up the brightness information and the color information of each pixel at a predetermined rate and synthesizes them. That is, the image processor relatively superimposes the elasticity image over the B-mode image in the same coordinate system. The image selection part, in response to a control command, selects an image to be shown on the display 112 from among a group of images stored in the frame memory. The display 112 has a monitor or the like on which to display the image data output from the image synthesize part 111.

As shown in FIGS. 7A and 7B, in this construction there is a tradeoff between artifact caused by a grating beam and the magnitude of error in the lateral direction of the displacement vector (the artifact mentioned here refers to a phenomenon in which a virtual image of an actually non-existent object emerges or one that, if a virtual image is not clearly recognizable, produces an effect of raising an acoustic noise base level to reduce a contrast resolution capability). That is, increasing the steering angle θ results in the artifact caused by the grading becoming large. On the other hand, as the steering angle θ decreases, the angle made by normals of the measured vectors also decreases, so that the positional accuracy of cross sections in the direction of measurement is degraded. FIG. 7A and FIG. 7B present a comparison between a case of a small steering angle and a case of a large steering angle. If the error of the measured vector is assumed to be ΔL (not dependent on the steering angle), the error in the lateral direction of the displacement vector obtained is 2ΔL/cos θ, which means that a decrease in θ results in an increased error. The sum of the error in the propagation direction and the error in the lateral direction is 2ΔL/cos θ+2ΔL/sin θ, which means that the total of errors becomes minimal when θ=45 degrees. (This is shown in FIG. 11. From this graph the limit of the steering angle can be determined.)

Therefore, optimizing the shape of the diameter weight of the transmission/reception beam for suppressing the grating is effective in balancing the above tradeoff.

One example method for suppressing the diameter weight of grating will be explained by referring to FIGS. 12 and 13A-13C. FIG. 12 shows shapes of three diameter weights: (a) one shown in a dashed line represents a case where the weight is constant (=1); (b) one shown in a solid line represents a case where the weight is a Gaussian function (exp(−$x^2$)); and (c) one shown in a dotted line represents a case where the weight is triangular-shaped on one side only. Each abscissa indicates "ch" numbers, in this case, ranging from 1 to 128. The ordinate represents a weight value, with the maximum value normalized to 1. It is assumed that the direction to which the beam is tilted is to the right side in the figure. Calculated results of beams using these three diameter weights (a), (b), (c) are shown in FIG. 13A, 13B and 13C, respectively. All these calculations were done under the condition of the central frequency of 7.5 MHz, device pitch of 0.24 mm, the focal distance of 3 cm, the beam steering angle of θ=30° and the ch number of 128. The abscissa represents the position in the lateral direction when observed on a plane 3 cm from the transducer. The ordinate represents the beam intensity in dB. Spiking at 20 mm is the original beam and what is seen at around −10 to −20 mm is the grating that is to be examined this time. Each of the figures is normalized to their maximum value. The maximum value of the grating varies among the FIGS. 13A, 13B and 13C. It is seen that the use of the one-side-triangle weight has reduced the grating by about 6 dB when compared with other standard weight functions. Generally, while it is difficult to reduce the entire energy of the grating, the maximum value can be reduced. By introducing asymmetry to (the shape of) the diameter weight, it can be made less likely to produce grating for the main beam.

Compared with the conventional elastic modulus imaging in one direction of displacement estimation, in the present embodiment, since an ultrasound is emitted in two or more directions, a frame rate is decreased. Particularly when an interval between the imaging of measured vector 1 and the imaging of measured vector 2 becomes long, the accuracy of the two-dimensional displacement vector may be degraded. FIG. 8 shows an example sequence of imaging the rasters of frame 1 and frame 2 alternately, with individual pulses assigned a number indicating the order of transmission. That is, the ultrasound transmit and receive part controls the sequence so as to radiate the pulses alternately to the plurality of frames. With this method, although the total frame rate is not improved, the time difference between the measurements of vector 1 and vector 2 can be reduced.

(Embodiment 2)

The present embodiment differs from embodiment 1 in the processing that is executed following the computation of the two-dimensional displacement vector. Other configurations are basically similar to those of embodiment 1. So, the following explanation will center on that difference.

In embodiment 1, the strain and the elastic modulus are determined by first calculating an absolute value of the displacement vector from a two-dimensional displacement vector. In the present embodiment, a strain vector processor 115 of FIG. 9 and a two-dimensional strain estimation process 211 of FIG. 10 determine the strain in two dimensions and have the two-dimensional strain visually represented. An anisotropy processor 117 visualizes the anisotropy of the strain (ratio between longitudinal strain and lateral strain). Since a living body is composed of various membranes in layers, there is a remarkable anisotropy in hardness between a direction along the membranes and a direction perpendicular to them. The arrangement of the present embodiment allows the anisotropic property to be visualized with high precision. Further, examining how layers are connected with each other in an image also allows the viewer to estimate how deeply a tumor infiltrates through other tissues.

While displacements are three-dimensional vector quantities, strains and stresses are 3×3 tensors. So it is difficult to determine all their components from an ultrasound B-mode image. If a third axis (a direction perpendicular to the ultrasound B-mode image) is assumed to have symmetry, the determining of two-dimensional strains accurately from the two-dimensional displacement vector is still difficult to achieve. In acquiring information on anisotropy of a living body, however, there is no need to determine a strain tensor because the strain anisotropy includes various kinds of information. Here, quantities obtained by differentiating the two-dimensional displacement vectors in a displacement direction are treated as approximated strain vectors. That is, instead of the displacement vectors (ΔLx, ΔLy), the strain vectors (ΔLx/Δx, ΔLy/Δy) are used and displayed or, from these ratios, information on anisotropy is visualized.

(Embodiment 3)

The present embodiment uses a two-dimensional array transducer to perform a three-dimensional imaging. To construct three measured vectors virtually not on the same plane, an imaging operation (transmission and reception of ultrasound) is done three times by directing a beam in three different steering angle directions. An intersection of each normal plane with respect to the three measured vectors constitutes a three-dimensional displacement vector. Processing, that is performed after a scalar of the three-dimensional displacement vector is taken as a displacement quantity, is the same as in embodiment 1. So its explanation is omitted. The three steering angles should be put as far apart from each other as possible to be able to minimize errors, for the same reason as explained in embodiment 1. It is also desired that the steering angles be selected in a way that can prevent a possible effect of grating from emerging.

One embodiment of the ultrasound diagnostic apparatus applying the present invention has been described. The ultrasound diagnostic apparatus applying this invention can be implemented in various other forms without departing from the spirit, and/or essential features, of this invention. The embodiments described above are therefore to be considered in all respects as illustrative and not restrictive.

While the above description has been made of some embodiments, it is apparent to those skilled in the art that the present invention is not limited to them but allows various changes and modifications to be made without departing from the spirit, and the scope of the appended claims, of this invention.

DESCRIPTION OF REFERENCE NUMERALS

Figure 1:
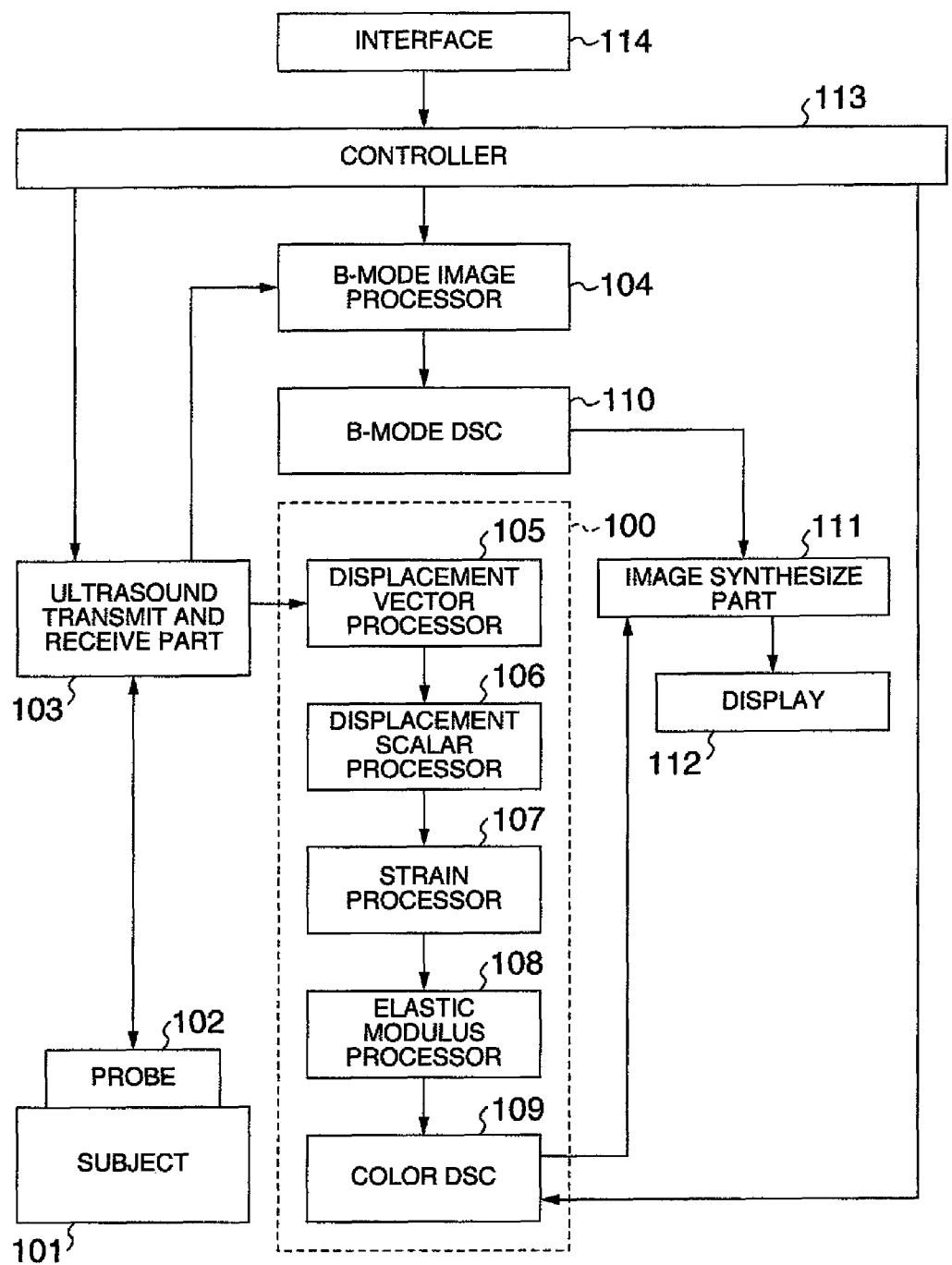
FIG. 1 is a block diagram of the apparatus in embodiment 1.
Figure 2:
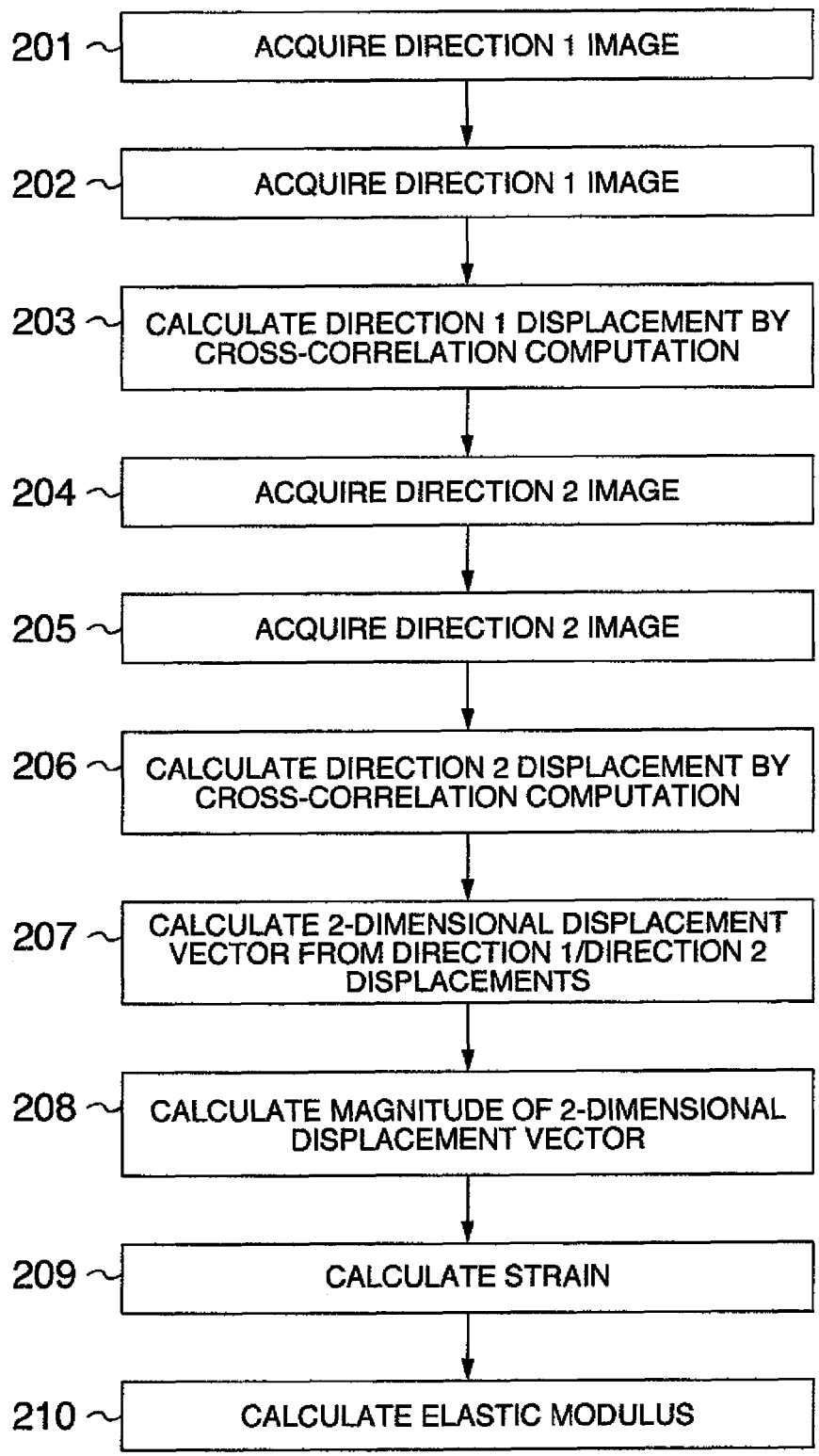
FIG. 2 is a process flow diagram in embodiment 1.
Figure 3A:
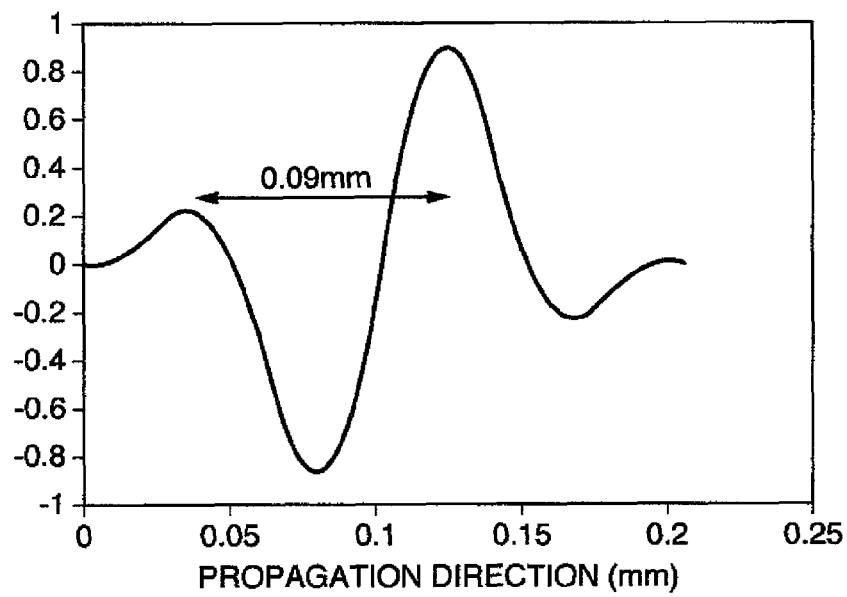
FIG. 3A is a point spread function with respect to a propagation direction and a lateral direction.
Figure 3B:
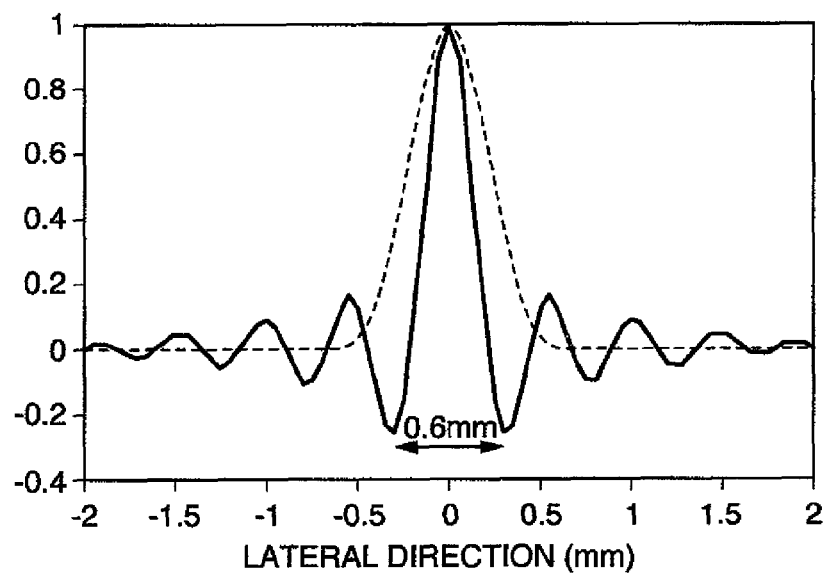
FIG. 3B is a point spread function with respect to a propagation direction and a lateral direction.
Figure 4A:
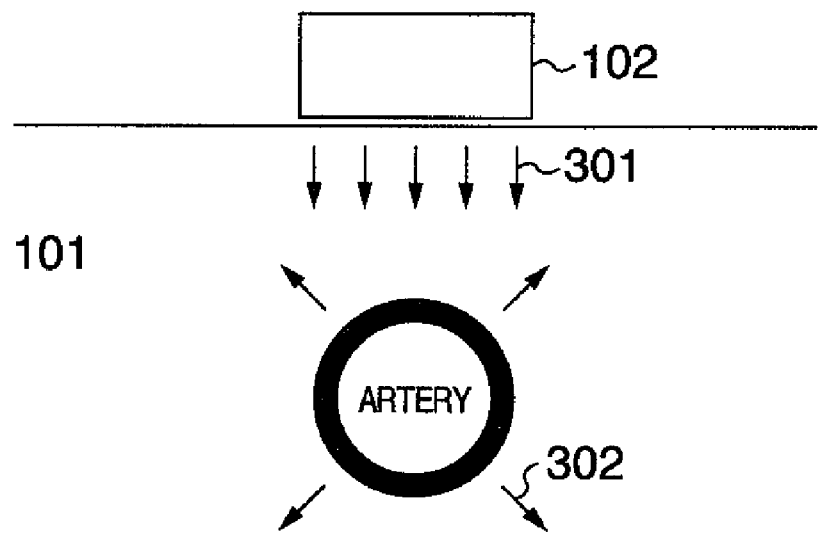
FIG. 4A is a diagram showing a relation between a displacement estimation direction and a tissue displacement direction.
Figure 4B:
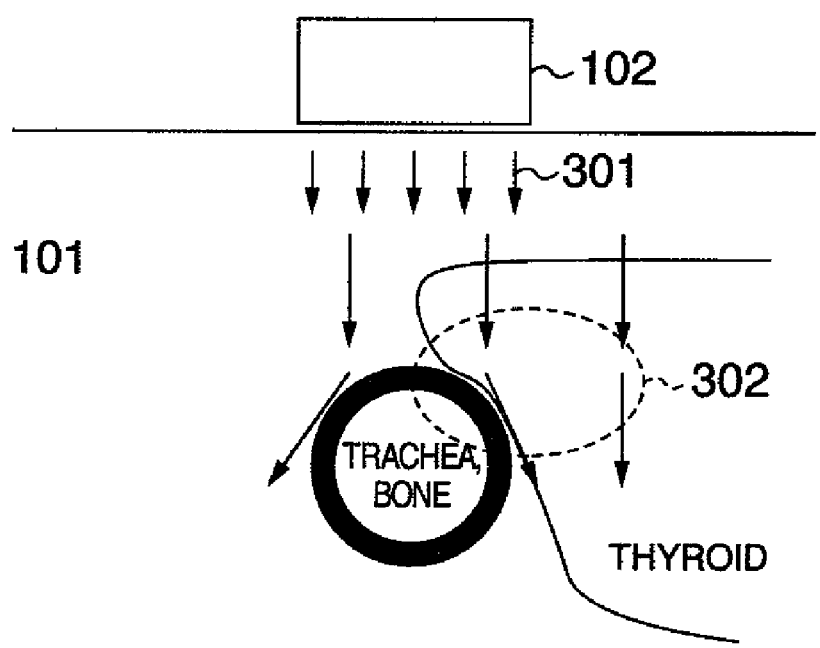
FIG. 4B is a diagram showing a relation between a displacement estimation direction and a tissue displacement direction.
Figure 5:
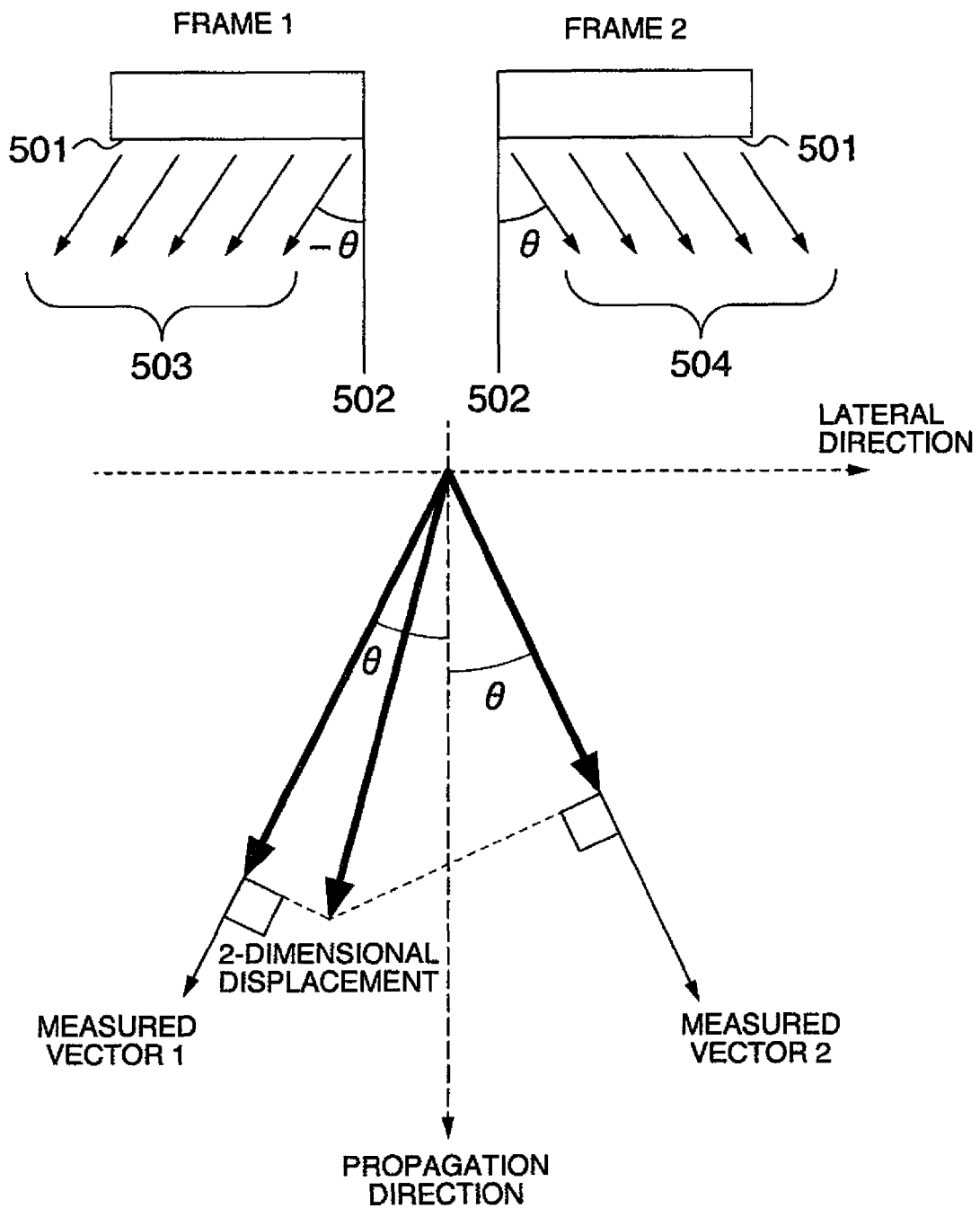
FIG. 5 is an explanatory diagram showing a method for calculating a two-dimensional displacement.
Figure 6:
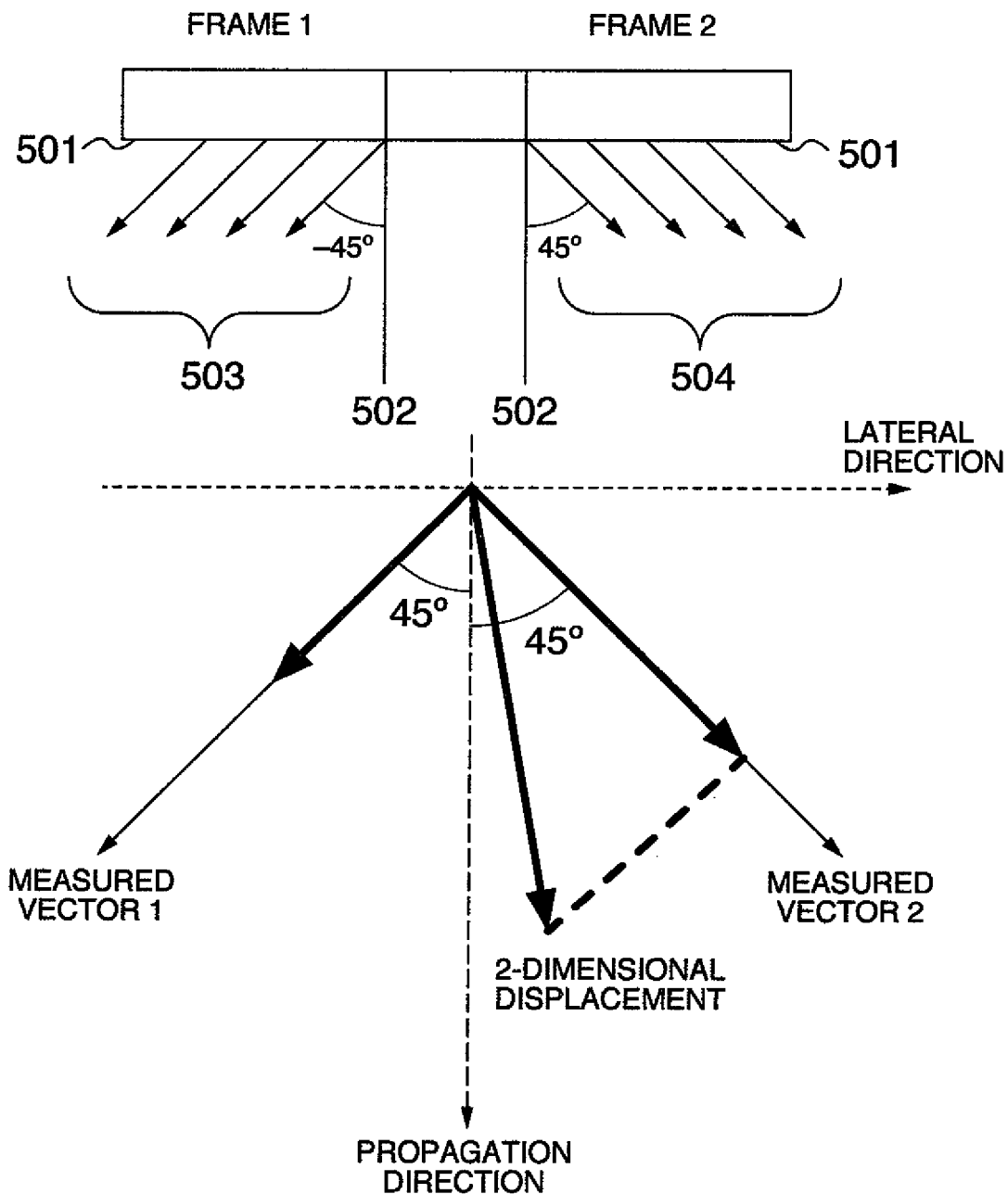
FIG. 6 is an explanatory diagram showing a method for calculating a two-dimensional displacement.
Figure 7A:
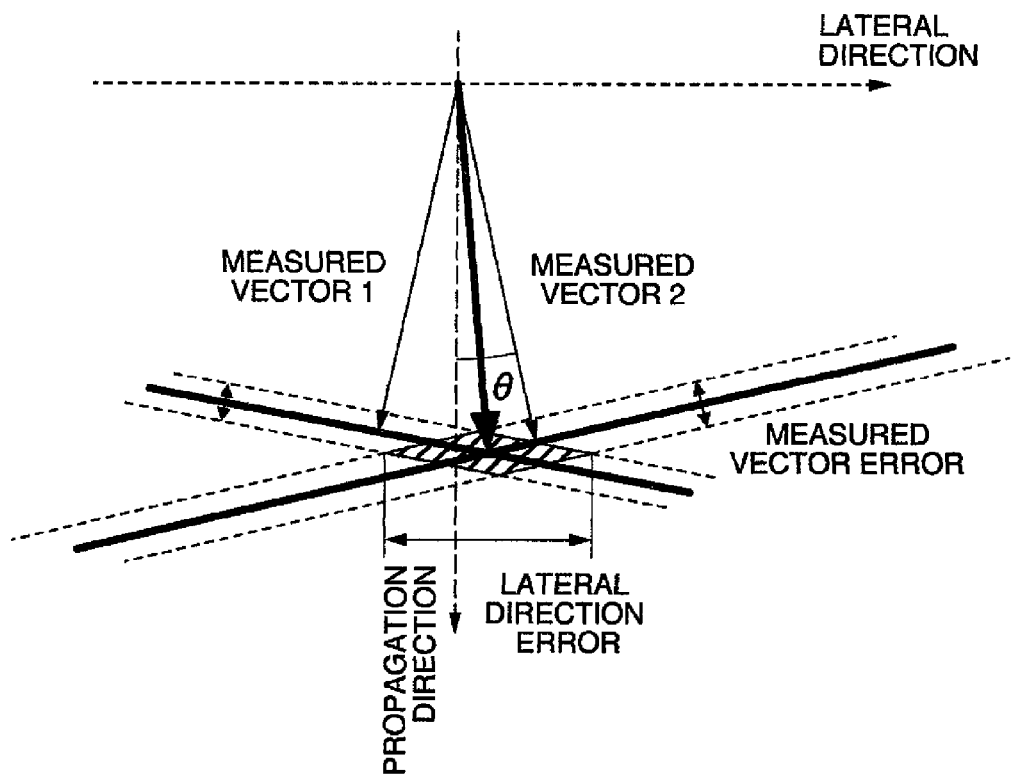
FIG. 7A is an explanatory diagram showing a method for calculating a two-dimensional displacement.
Figure 7B:
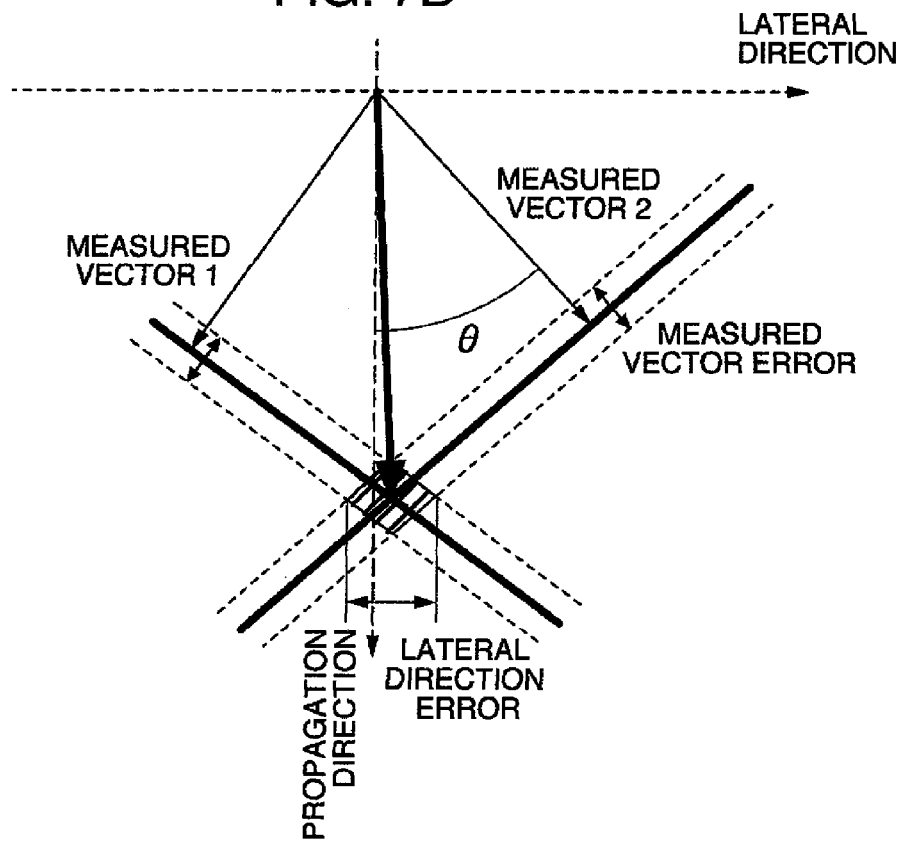
FIG. 7B is an explanatory diagram showing a method for calculating a two-dimensional displacement.
Figure 8:
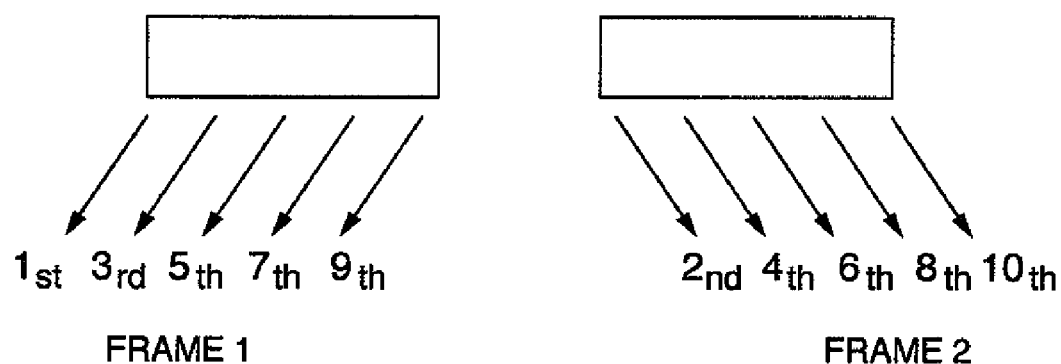
FIG. 8 is an explanatory diagram of a transmission sequence.
Figure 9:
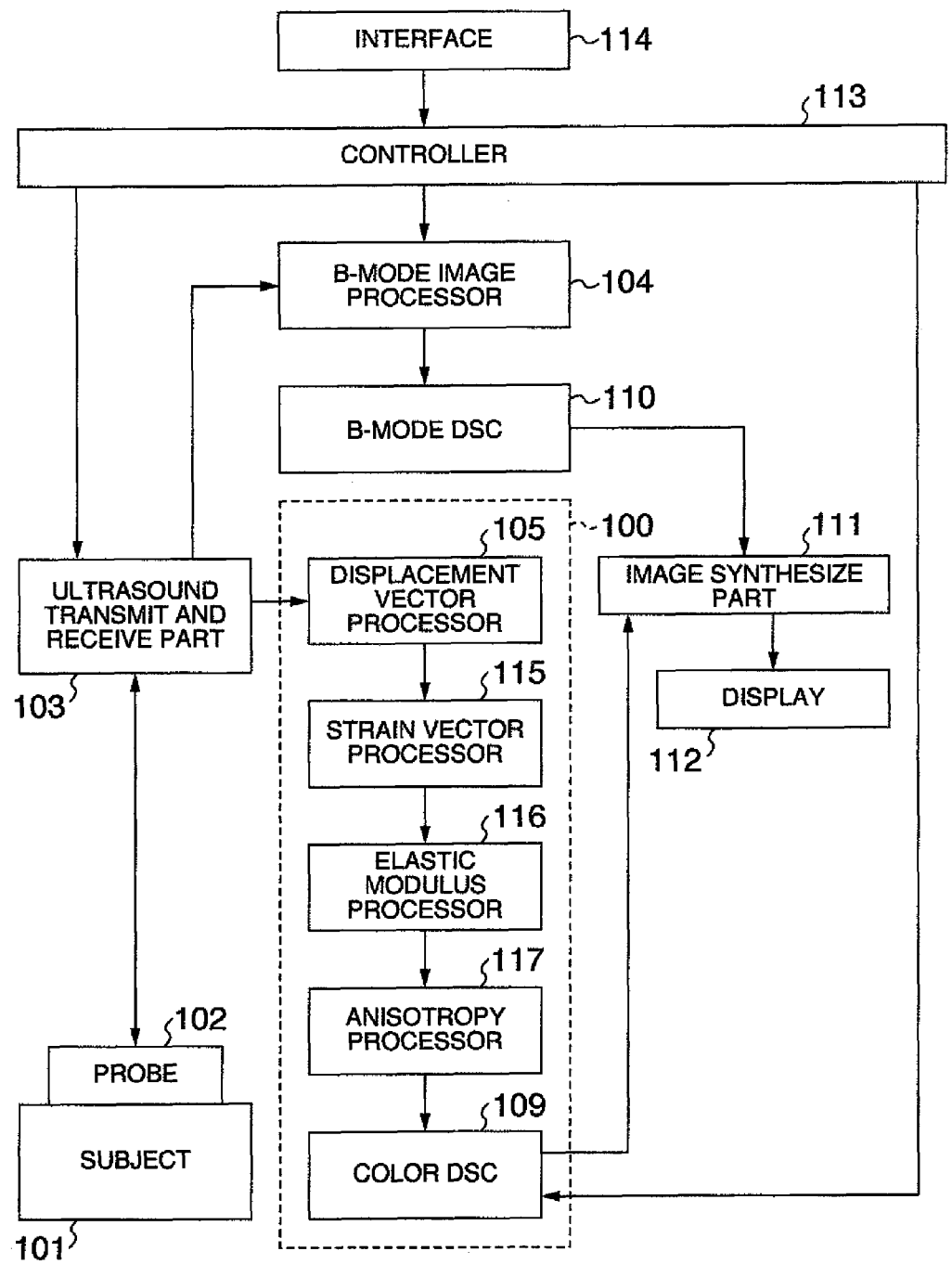
FIG. 9 is a block diagram for an apparatus of embodiment 2.
Figure 10:
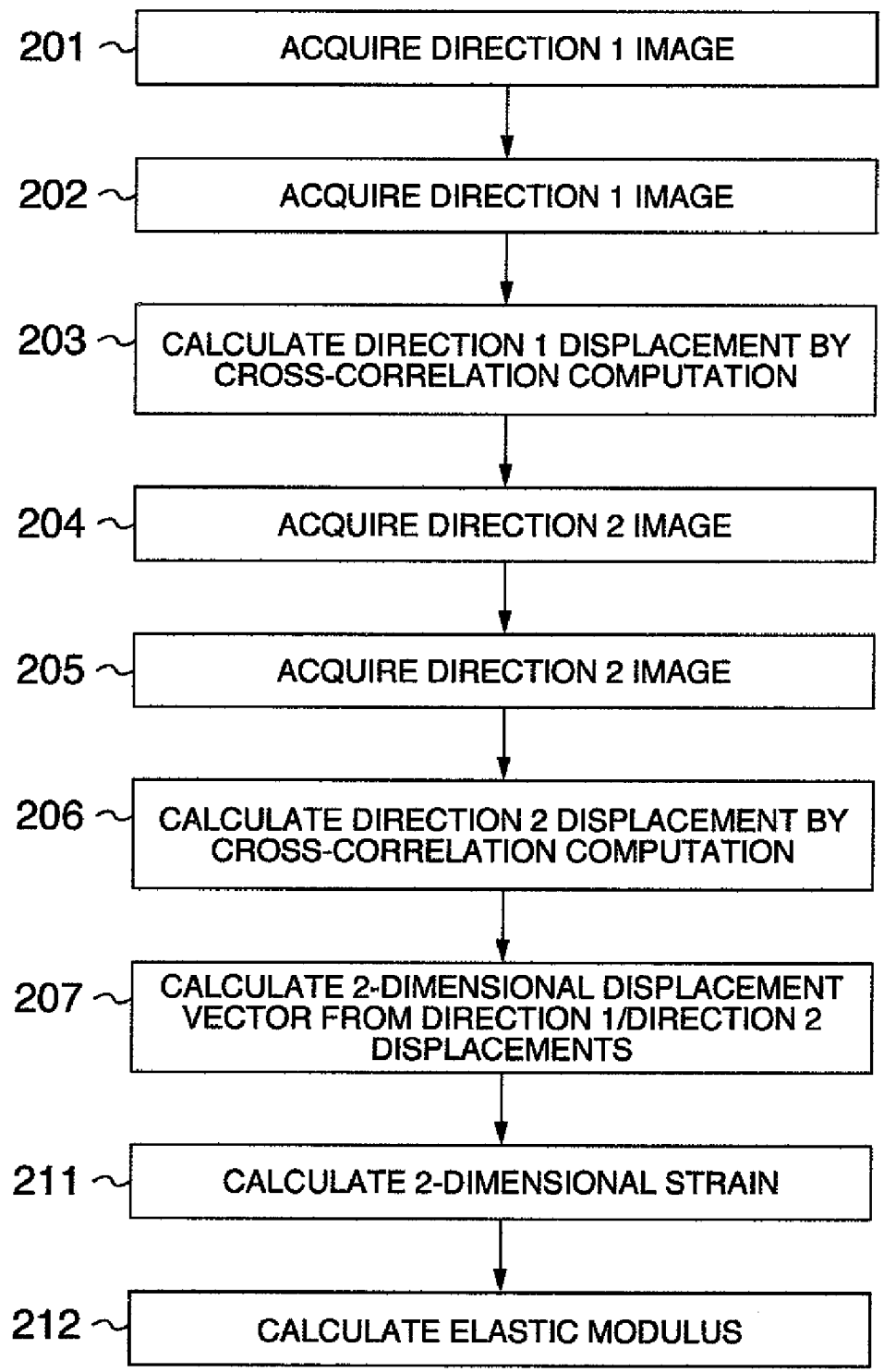
FIG. 10 is a process flow diagram in embodiment 2.
Figure 11:
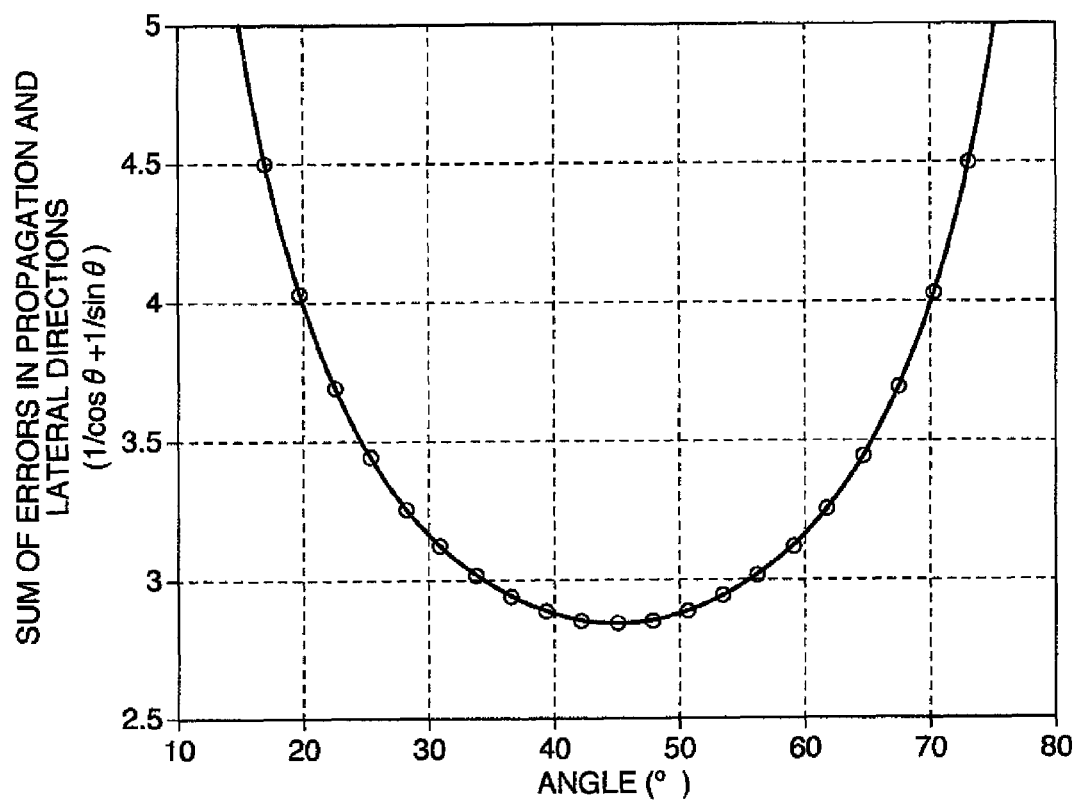
FIG. 11 is an explanatory diagram showing a steering angle.
Figure 12:
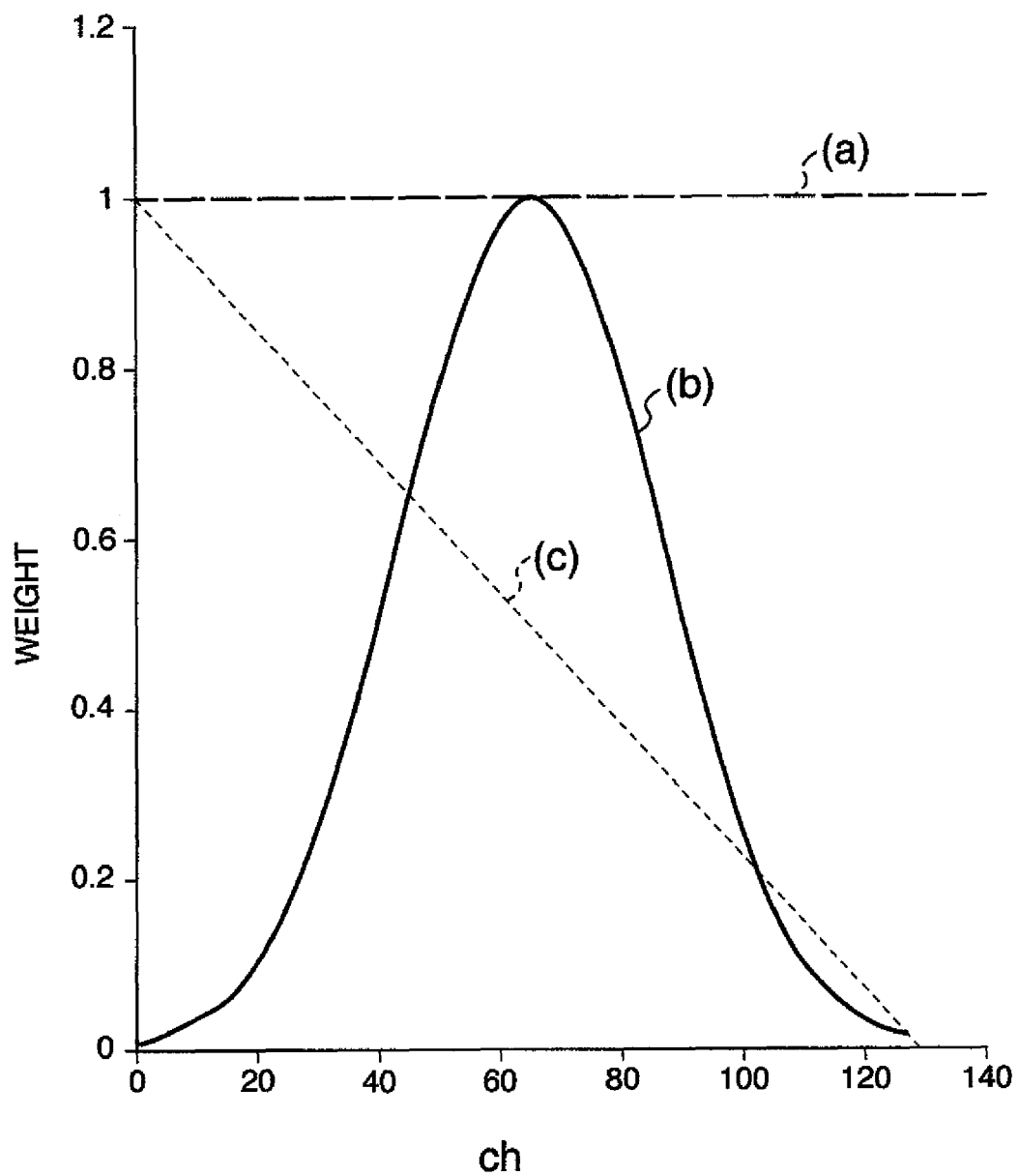
FIG. 12 is a diagram showing an example method for suppressing a diameter weight of grating.
Figure 13A:
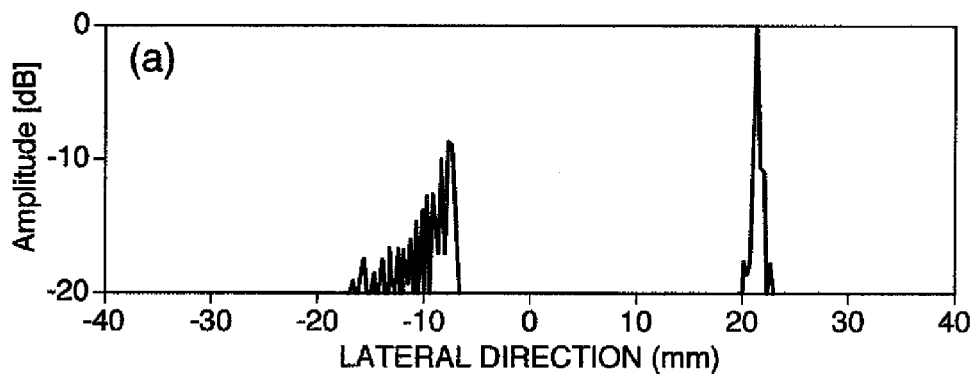
FIG. 13A is a diagram showing an example method for suppressing a diameter weight of grating.
Figure 13B:
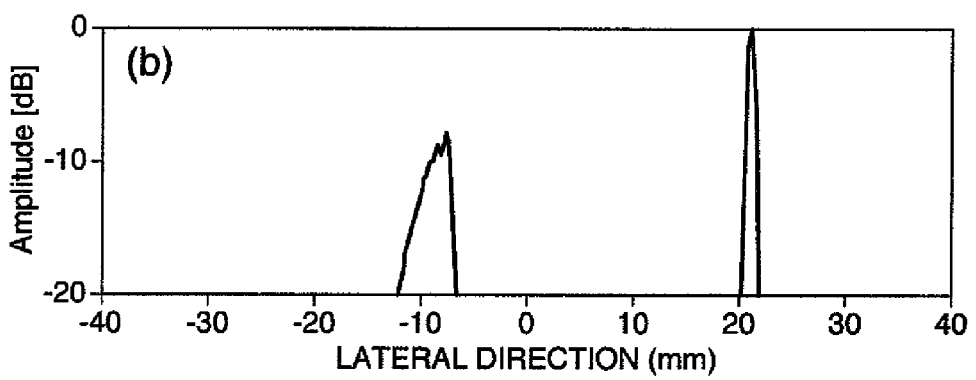
FIG. 13B is a diagram showing an example method for suppressing a diameter weight of grating.
Figure 13C:
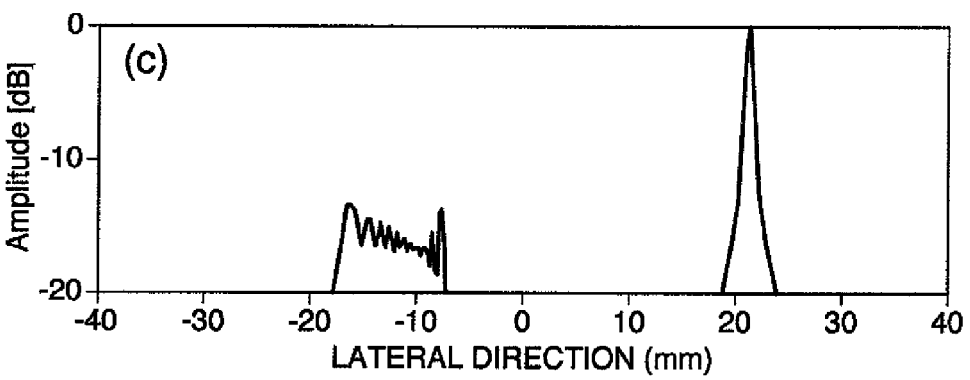
FIG. 13C is a diagram showing an example method for suppressing a diameter weight of grating.

100 . . . elasticity image processor, 101 . . . subject, 102 . . . probe, 103 . . . ultrasound transmit and receive part, 104 . . . B-mode image processor, 105 . . . displacement vector processor, 106 . . . displacement scalar processor, 107 . . . strain processor, 108 . . . elasticity processor, 109 . . . color DSC, 110 . . . B-mode DSC, 111 . . . image synthesize part, 112 . . . display, 113 . . . controller, 114 . . . interface, 115 . . . strain vector processor, 116 . . . elastic modulus vector processor, 117 . . . anisotropic parameter processor, 201 . . . step for acquiring image in lateral direction 1, 202 . . . step for acquiring image in lateral direction 1, 203 . . . step for calculating displacement in direction 1 by cross-correlation computation, 204 . . . step for acquiring image in lateral direction 2, 205 . . . step for acquiring image in lateral direction 2, 206 . . . step for calculating displacement in direction 2 by cross-correlation computation, 207 . . . step for calculating two-dimensional displacement vector based on displacements in direction 1 and direction 2, 208 . . . step for calculating magnitude of absolute value of two-dimensional displacement vector, 209 . . . step for calculating strain, 210 . . . step for calculating elastic modulus, 211 . . . step for calculating two-dimensional strain, 212 . . . step for calculating two-dimensional elastic modulus, 301 . . . displacement estimation direction, 302 . . . tissue displacement direction.

The invention claimed is:

1. An ultrasonograph comprising:
an ultrasound probe to emit an ultrasound in a plurality of directions against a subject, the plurality of directions including a first measurement direction and a second measurement direction, where the first measurement direction is disposed in a first direction relative to a lateral direction and a propagation direction defined by the ultrasonic probe, and the second measurement direction is disposed in a second direction relative to the lateral direction and the propagation direction, where the second measurement direction is different from the first measurement direction;
an ultrasound transmit and receive part to control the ultrasound probe to perform a plurality of transmissions and receptions of the ultrasound in each of the first measurement direction and the second measurement direction;
a displacement vector processor configured to:
calculate a displacement estimation vector in each of the first measurement direction and the second measurement direction, using a result of the plurality of transmissions and receptions of the ultrasound, and
calculate a displacement vector based on the displacement estimation vectors;
a strain processor to calculate strain information of the subject based on the displacement vector;
an image data generator to create image data based on the calculated strain information; and
a display to display an image based on the image data.

2. An ultrasonograph according to claim 1, further comprising:
an elasticity processor to calculate elasticity information on the subject, based on the strain information;
wherein the image data generator generates the image data based on the elasticity information.

3. An ultrasonograph according to claim 1, wherein the ultrasound transmit and receive part performs a control to execute a first transmission and reception corresponding to the ultrasound emitted before the ultrasound probe is pressed against the subject and a second transmission and reception corresponding to the ultrasound emitted after the ultrasound probe is pressed against the subject;
wherein the displacement vector processor calculates displacements before and after the pressing of the probe against the subject.

4. An ultrasonograph according to claim 1, wherein the displacement vector processor adds up the displacement estimation vectors measured from each of the first measurement direction and the second measurement direction to determine the displacement vector.

5. An ultrasonograph according to claim 1, wherein the plurality of directions are three measurement directions which are in mutually differing directions from each other.

6. An ultrasonograph according to claim 1, wherein the displacement vector processor calculates two-dimensional displacement vectors or three-dimensional displacement vectors as the displacement vector.

7. An ultrasonograph according to claim 1, wherein the displacement vector processor calculates two-dimensional displacement vectors or three-dimensional displacement vectors as the displacement vector, and the strain processor calculates an absolute value of the displacement from the two-dimensional displacement vectors or the three-dimensional displacement vectors.

8. An ultrasonograph according to claim 1, wherein the displacement vector processor calculates two-dimensional displacement vectors or three-dimensional displacement vectors as the displacement vector, and the strain processor differentiates each of the two-dimensional displacement vectors in a displacement direction.

9. An ultrasonograph according to claim 1, wherein the displacement vector processor calculates two-dimensional displacement vectors or three-dimensional displacement vectors as the displacement vector, and strain processor differentiates the two-dimensional displacement vectors or the three-dimensional displacement vectors in a displacement direction to determine strain vectors.

10. An ultrasonograph according to claim 1, wherein the ultrasound probe is a two-dimensional array transducer that transmits and receives the ultrasound in a plurality of different steering angle directions.

11. An ultrasonograph according to claim 1, wherein the ultrasound transmit and receive part performs a control to emit the ultrasound alternately to frames corresponding to each of the first measurement direction and the second measurement direction.

12. An ultrasonograph according to claim 1, wherein the displacement vector processor calculates the displacement vector as a vector having its end point at an intersection of line segments extending perpendicular to each of the displacement estimation vectors measured in each of the first measurement direction and the second measurement direction.

13. An ultrasonograph according to claim 1, wherein the ultrasound transmit and receive part performs a control to deflect the ultrasound when transmitting and receiving it to and from the subject.

14. An ultrasonograph according to claim 1, wherein an angle formed by a direction perpendicular to a surface of a device making up the ultrasound probe which faces the subject and by one of the first measurement direction and the second measurement direction, is less than 45 degrees.

15. An ultrasonograph according to claim 1, wherein an angle formed by a direction perpendicular to a surface of a device making up the ultrasound probe which faces the subject and by one of the first measurement direction and the second measurement direction, is from 20 degrees to 30 degrees.

16. An ultrasonograph according to claim 1, wherein the ultrasound transmit and receive part makes asymmetric the shape of a diameter weight of the ultrasound beam to be transmitted and received.

17. An ultrasonograph comprising:
an ultrasound probe to steer an ultrasound in a plurality of steered directions against a subject, where each of the plurality of steered directions is relative to a lateral direction and a propagation direction defined by the ultrasonic probe, and where the plurality of steered directions are steered in mutually differing directions from each other;
an ultrasound transmit and receive part to control the ultrasound probe to perform a plurality of transmissions and receptions of the ultrasound in each of the plurality of steered directions;
a displacement vector processor configured to:
calculate a displacement estimation vector in each of the plurality of steered directions from a result of the plurality of transmissions and receptions of the ultrasound, and
calculate a displacement vector based on the displacement estimation vectors;
a strain processor to calculate strain information of the subject based on the displacement vector;
an image data generator to create image data based on the calculated strain information; and
a display to display an image based on the image data.

* * * * *